Figure 1:
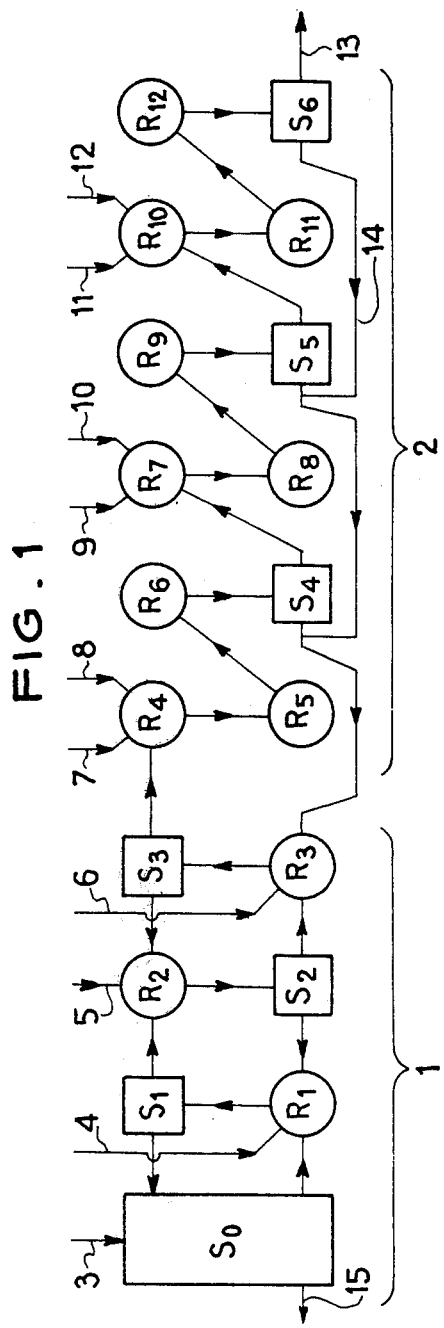

United States Patent [19]

de Cazenove et al.

[11] 4,022,844
[45] May 10, 1977

[54] PROCESS FOR CONTINUOUS PRODUCTION OF TRINITROTOLUENE

[75] Inventors: Hubert E. de Cazenove, Paris; Daniel Doyen, Sorgues; Jacques M. Dussidour; Jean-Jacques Gautier, both of Saint Chamas, all of France

[73] Assignee: Societe Nationale des Poudres et Explosifs, France

[22] Filed: Feb. 20, 1973

[21] Appl. No.: 334,007

[30] Foreign Application Priority Data

Feb. 25, 1972  France .............................. 72.06415

[52] U.S. Cl. .................................. 260/645; 23/266
[51] Int. Cl.² ........................................ C07C 79/10
[58] Field of Search .................................... 260/645

[56] References Cited
UNITED STATES PATENTS 2,951,746  9/1960  Kouba et al. .................. 260/645 X
3,204,000  8/1965  Samuelsen ......................... 260/645

FOREIGN PATENTS OR APPLICATIONS 539,095  4/1957  Canada ............................. 260/645
772,895  4/1957  United Kingdom ............... 260/645
834,260  5/1960  United Kingdom ............... 260/645

Primary Examiner—Leland A. Sebastian
Attorney, Agent, or Firm—Bucknam and Archer

[57] ABSTRACT

An improved process for the continuous production of trinitrotoluene by dinitrating and trinitrating mononitrotoluene in the presence of concentrated nitric acid and concentrated sulphuric acid or fuming sulphuric acid, which is characterised in that the trinitration step is carried out in a group of pieces of equipment in which the reagents flow in co-current, this group comprising at least two stages, each stage having at least two nitration reactors in series followed by a separator and the first of the reactors in each stage being supplied separately with a mixture of concentrated sulphuric acid or fuming sulphuric acid and nitric acid.

Installations for carrying out this process are also disclosed.

7 Claims, 5 Drawing Figures

PROCESS FOR CONTINUOUS PRODUCTION OF TRINITROTOLUENE

This invention is concerned with a process and installation for the continuous production of trinitrotoluene by dinitration followed by trinitration, of mononitrotoluene in the presence of concentrated nitric acid and concentrated sulphuric acid or fuming sulphuric acid.

Trinitrotoluene, also known by the name of "tolite", is an explosive commonly employed in military applications. It is known to prepare it continuously from mononitrotoluene, nitric acid and approximately 96% concentrated sulphuric acid. The installation used for carrying out this manufacturing process comprises a series of nitration reactors and separators. Mononitrotoluene is introduced at one end of the installation, sulphuric acid is introduced at the other end so as to flow counter-currently to the mononitrotoluene, and nitric acid is fed into the nitration reactors. Irinitrotoluene is collected in the last separator situated at the end opposite to that where mononitrotoluene is introduced and the residual nitric and sulphuric acids are recovered in the first separator situated at the other end of the installation.

In order to obtain a product which can be used directly, this process requires an installation comprising approximately 16 reactors and 16 separators.

This process has a number of disadvantages, some of which are characteristic of any operation in which the reagents flow in counter-current. More particularly, the flow rates of the respective reagents tend to fluctuate, the separation of the reagents by decantation in the separators is not always satisfactory, and it is impossible in the present case, to stir or cool the reagents in the separators. These factors make it necessary to keep the concentration of nitric acid in the separators at a relatively low value, which is prejudicial to the overall yield of the process.

It is also known that the presence of water, which is inevitable when sulphuric acid is used, makes it possible to trinitrotoluene oxidation reactions to take place in the nitration reactors. It is therefore necessary to reduce the dwell time of dinitrotoluene to the minimum necessary to enable the conversion reaction to trinitrotoluene to take place. However, this is achieved very inadequately in counter-current processes and, in the present case, a large proportion of the trinitrotoluene formed is continuously recycled from one apparatus to another, which considerably increases the contact time between the trinitrotoluene and sulphuric acid. The oxidation products formed are known as "compounds" and consist predominantly of the dimer of trinitrobenzoic acid.

Another known process for the production of trinitrotoluene comprises nitrating mononitrotoluene in the presence of fuming sulphuric acid with the reagents flowing in counter-current as in the above-mentioned process. This process enables the number of items of equipment in the installation to be reduced, but has the disadvantages of countercurrent processes mentioned above.

Another variant of the process for the production of trinitrotoluene is also known, in which fuming sulphuric acid is used and in which the reagents flow in co-current. This process enables trinitrotoluene to be produced under suitable conditions, but, as in all processes employing fuming sulphuric acid, it has the disadvantage of yielding large amounts of residual nitric and sulfuric acids which are not easy to re-use.

Whatever process is used, the trinitrotoluene obtained always contains 4.5% of trinitrotoluene isomers, which have the effect of lowering the melting point by approximately 2.5° C. Trinitrotoluene is purified by means of sodium sulphite in accordance with two well known processes, namely treatment with fused sulphite or treatment with crystalline sulphite. The latter process is more effective, particularly because it enables practically all the impurities, with the exception of dinitrotoluene, to be removed from the trinitrotoluene, but it is expensive; on the other hand, treatment with fused sulphite does not remove certain impurities, such as the hydrolysis products of the "white bodies".

The above-mentioned processes using sulphuric acid do not enable grade I trinitrotoluene (melting point of 80.2° C) to be obtained consistently after treatment with fused sulphite, so that treatment with crystalline sulphite is necessary.

On the other hand, the known processes using fuming sulphuric acid enable grade I trinitrotoluene to be obtained after treatment with fused sulphite.

We have now devised a process for the continuous production of trinitrotoluene which can be carried out with a relatively small number of pieces of equipment, while at the same time giving a grade I product in good yeild after simple treatment with fused sulphite, the process being operable, with minimum modifications, either with concentrated sulphuric acid or with fuming sulphuric acid.

According to the present invention, therefore, we provide a process for the continuous production of trinitrotoluene by dinitrating and trinitrating mononitrotoluene in the presence of concentrated nitric acid and concentrated sulphuric acid or fuming sulphuric acid, in which the trinitration step is carried out in a group of pieces of equipment in which the reagents flow in co-current, this group comprising at least two stages, each stage having at least two nitration reactors in series followed by a separator and the first of the reactors of each stage being supplied separately with a mixture of concentrated sulphuric acid or fuming sulphuric acid and nitric acid.

Each trinitration stage must, in effect, comprise a minimum of two nitration reactors arranged in series with a separator in order to be certain that the trinitration reaction does not continue in the separator, which would be hazardous. By using at least two nitration reactors in series before a separator, we have found that the reaction mixture present in the reactor which precedes the separator is sufficiently depleted in nitric acid for only an acceptable amount of nitric acid to be introduced into the separator. By supplying the first reactor of each trinitration stage individually with a mixture of sulphuric acid or fuming sulphuric acid and nitric acid, the total amount of nitric acid and sulphuric acid or fuming sulphuric acid required is distributed among several reactors and excesses or deficiencies of acid in one or other of these reactors is thus avoided. Excess nitric acid in the reactor can cause a continuation of the nitration reaction in the adjacent separator and excess sulphuric acid can cause a part of the trinitrotoluene formed to dissolve, so that it no longer separates out in the separator. A deficiency of nitric acid or of sulphuric acid in a given reactor causes the overall yield of the process to be reduced. This distribution of the inputs also permits better separation in the separators by reducing the flow rates.

The dinitration step is carried out in known manner in a group of pieces of equipment comprising at least three stages, each stage having a nitration reactor and a separator, in which mononitrotoluene and dinitrotoluene flow in countercurrent relative to the mixture of sulphuric acid or fuming sulphuric acid and nitric acid. These three stages of the dinitration step consist of a stage of cooling the reagents, a stage of starting the dinitration, and an actual dinitration stage.

The reagents are cooled by circulating cold water in a coil located in a reactor of the cooling stage. Likewise, the starting of the dinitration and the actual dinitration of mononitrotoluene are carried out by separately introducing 50–55% aqueous nitric acid into a reactor of each starting stage of the dinitration and of each actual dinitration stage.

According to a preferred feature of the invention, the mixture of nitric acid and sulphuric acid which separates out in the separators of each trinitration stage is recycled to the last reactor of the dinitration step.

The nitric acid used to supply the trinitration reactors preferably has a concentration of at least 98% by weight and the concentrated sulphuric acid used preferably has a concentration of at least 96% by weight. When concentrated sulphuric acid is used, the trinitration step preferably comprises at least 3 stages.

When fuming sulphuric acid is used instead of sulphuric acid, the trinitration step can comprise only two stages, but the nitric acid and the fuming sulphuric acid must be introduced separately into a mixer before introducing the mixture of them into the first reactor of each trinitration stage.

According to another preferred feature of the invention, the rate at which sulphuric acid or fuming sulphuric acid and nitric acid are supplied to the first reactor of the first trinitration stage is approximately equal to the sum of the rates at which sulphuric acid or fuming sulphuric acid and nitric acid are supplied to the reactors of the other stages. This condition permits optimum distribution of the inputs to the various trinitration reactors.

It is also advantageous to limit the weight concentration of nitric acid in the sulphuric acid/nitric acid supply mixture to a value of from 8 to 15% in order that the concentration of nitric acid in the separators shall not be greater than 5%. As has been stated previously, this limit to the concentration of nitric acid prevents the nitration reaction from continuing in the separators.

The present invention also comprises an installation for carrying out the process according to the invention, which comprises two sections, the first consisting of a group of pieces of equipment comprising at least three stages, each stage having a nitration reactor and a separator in which, in use, mononitrotoluene and dinitrotoluene flow in counter-current relative to the mixture of sulphuric acid or fuming sulphuric acid and nitric acid, and the second consisting of a group of pieces of equipment in which, in use, the reagents flow in co-current, this group comprising at least two stages, each stage having at least two nitration reactors in series followed by a separator and the first of the reactors of each stage having means for the separate supply of a mixture of sulphuric acid or fuming sulphuric acid and nitric acid.

Figure 2:
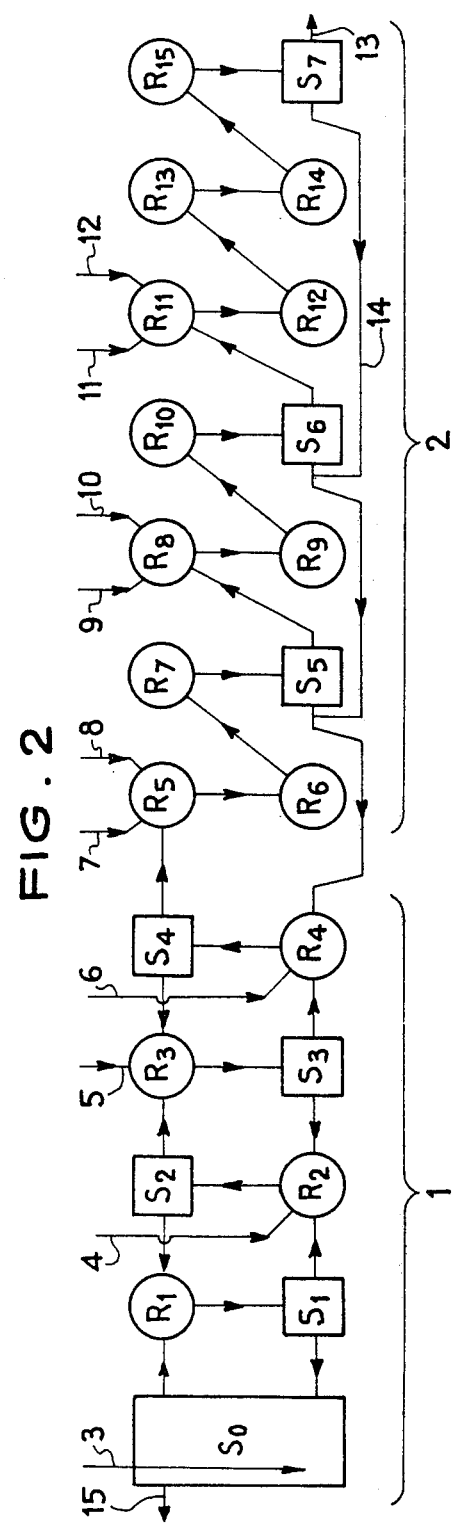
Figure 3:
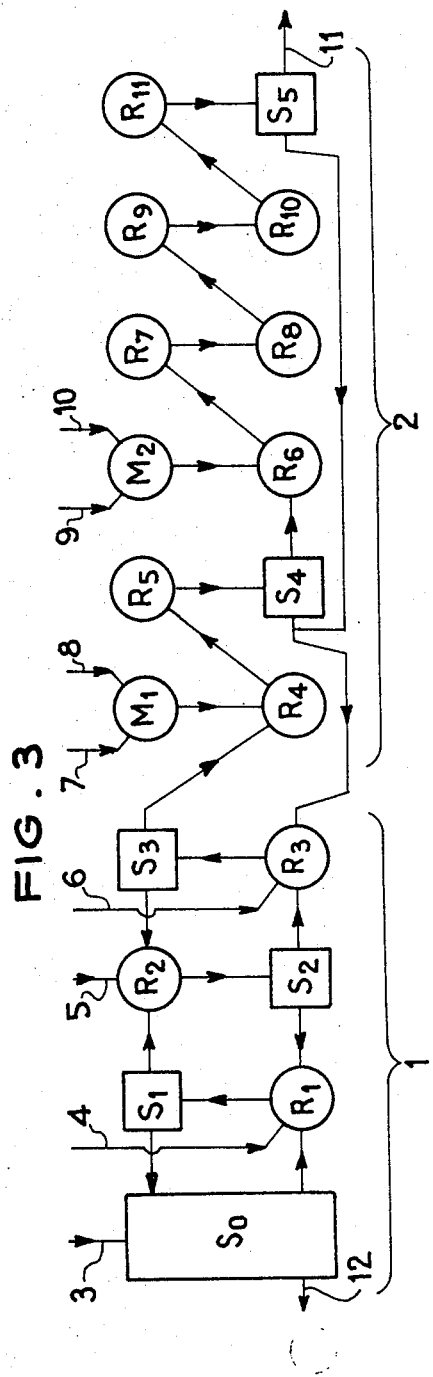
Figure 4:
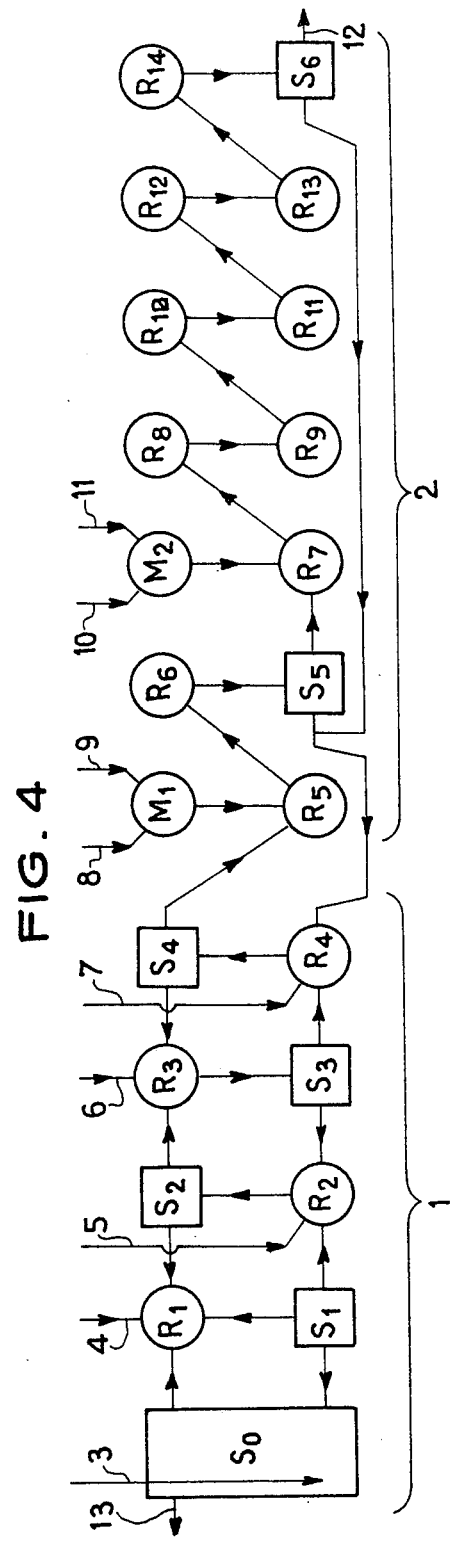
Figure 5:
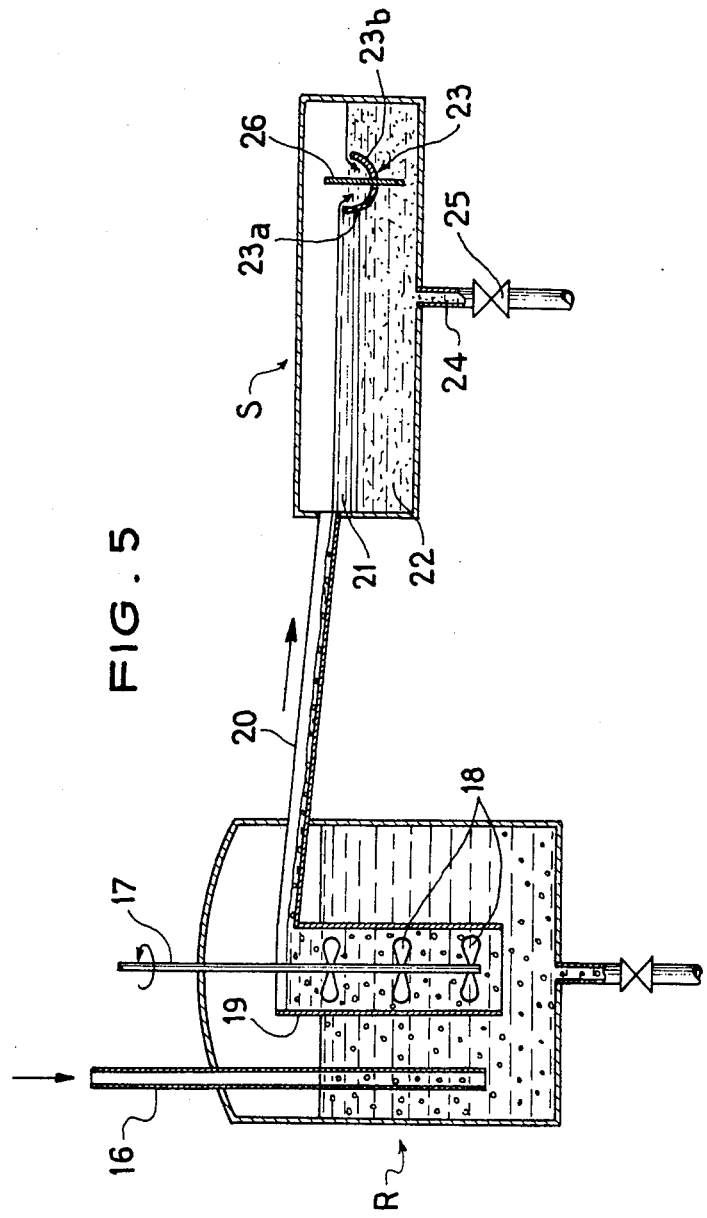

In order that the invention may be more fully understood, preferred embodiments of the installation according to the invention, and the operation thereof, will now be described, by way of example only, with reference to the accompanying drawings, in which:

FIG. 1 is a schematic view of an installation for carrying out the process according to the invention using concentrated sulphuric acid, FIG. 2 is a schematic view of a variant of the installation of FIG. 1, FIG. 3 is a schematic view of an installation for carrying out the process using fuming sulphuric acid, FIG. 4 is a schematic view of a variant of the installation of FIG. 3, and FIG. 5 is a schematic view of a reactor equipped with a central column containing a propeller, this reactor being connected to a separator.

Referring to FIGS. 1 – 4, it will be seen that installations for carrying out the process comprise two sections, namely a section 1 for carrying out the dinitration step which itself comprises a stage of cooling the reagents, of starting the dinitration and of dinitrating mononitrotoluene, which is introduced at 3 into the separator $S_0$, and a section 2 for carrying out the trinitration step.

Referring to FIG. 1, section 2 for carrying out the trinitration step comprises a group of pieces of equipment in which $R_4$ is a reactor and $S_4$ a separator, in which the reagents flow in cocurrent. This trinitration section 2 comprises at least two stages, and preferably three, as shown in FIG. 1, when sulphuric acid is used, each stage having at least two nitration reactors, or three as in the example of FIG. 1, such as $R_4$, $R_5$ and $R_6$ in series followed by a separator such as $S_4$. The first of the reactors of each stage, that is to say the reactors $R_4$, $R_7$ and $R_{10}$ as shown in FIG. 1 are supplied separately with a mixture of sulphuric acid and nitric acid.

The dinitration step is carried out in a group of pieces of equipment comprising at least three stages, each stage having a nitration reactor $R_1$, $R_2$ or $R_3$, and a separator $S_1$, $S_2$ or $S_3$, in which mononitrotoluene and dinitrotoluene flow in countercurrent relative to the mixture of sulphuric acid and nitric acid.

The three stages of the dinitration section 1 consist of a stage of cooling the acids used, a stage of starting dinitration and a dinitration stage.

The stage of cooling and diluting the reagents comprises a reactor $R_1$ and a separator $S_1$, the reagents being cooled by circulating cold water in a coil (not shown) located inside the reactor $R_1$.

The starting stage of the dinitration consists of the reactor $R_2$ and the separator $S_2$, the start of dinitration being brought about by introducing 50 – 55% aqueous nitric acid into the reactor $R_2$, at 5. The actual dinitration of mononitroluene to dinitrotoluene is completed in the adjacent stage which consists of a reactor $R_3$ and a separator $S_3$ and is effected by introducing 50 – 55% aqueous nitric acid into the reactor $R_3$, at 6. The dinitrotoluene formed in the reactor $R_3$ and then separated from the acids in the separator $S_3$ is then introduced into the first trinitration reactor $R_4$ of the first trinitration stage. The trinitration reactor $R_4$ is supplied, at 7, with sulphuric acid having a concentration of at least 96% by weight, and at 8, with nitric acid having a concentration of at least 98% by weight. The trinitration reaction continues in the reactors $R_5$ and $R_6$ and the trinitrotoluene formed, and the dinitrotoluene which has not been converted to trinitrotoluene, are separated out in the separator $S_4$.

Trinitration is completed in the following stages, in which the reactors $R_7$ and $R_{10}$ are also supplied, at 9 and 11, with sulphuric acid, and at 10 and 12, with nitric acid. The trinitrotoluene is recovered at 13 after being separated out in the separator $S_6$.

The rate at which sulphuric acid and nitric acid are supplied to the first reactor $R_4$ of the first trinitration stage is preferably equal to the sum of the rates at which sulphuric acid and nitric acid are supplied to the reactors $R_7$ and $R_{10}$ of the following stages.

It is also advantageous to limit the concentration of nitric acid in the sulphuric acid/nitric acid mixture which is supplied to the reactors $R_4$, $R_7$ and $R_{10}$ from 8 to 15% by weight in order that the concentration of nitric acid in the separators shall not be greater than 5% and in order to prevent the nitration reaction from continuing in the separators $S_4$, $S_5$ and $S_6$.

The nitric acid which has not reacted with the dinitrotoluene and the residual sulphuric acid are separated in each of the separators $S_4$, $S_5$ and $S_6$. These acids are recycled to the last reactor $R_3$ of the dinitration stage, flowing in countercurrent relative to the dinitrotoluene formed in the reactors $R_3$ and $R_2$ and to the mononitrotoluene introduced into the separator $S_0$, and are then separated out in the latter. The acids are recovered at the outlet of the separator $S_0$ and can be re-used in the production of mononitrotoluene and then subjected to a denitration treatment and a reconcentration treatment to obtain 96% sulphuric acid.

The last reactor of each stage of each of the sections 1 and 2 contains means for directing flow of the reagents in a particular direction.

Such a means is shown in FIG. 5 which shows a reactor R connected to a separator S. The means for directing flow of the reagents introduced via the conduit 16 into the reactor R to the separator S consists of a central rod 17 carrying a series of propellers 18 located in a central vertical cylinder 19. The reaction mixture in the reactor R is stirred and raised by the pumping action in the vertical cylinder and overflow at the top of the cylinder through a conduit 20 to the separator S. The pumping action also causes the reaction mixture to flow in the adjacent pieces of equipment. The reaction mixture is cooled, if necessary, by a cold water coil placed outside the cylinder.

The reaction mixture separates in the separator S into two layers 21 and 22, the upper layer 21 consisting of the nitro derivatives of toluene which are passed on to the reactor of the following stage. For this purpose, the separator S contains a channel 23 with a longitudinal partition 26 which divides the channel into two half-channels 23a and 23b. The half-channel 23a situated on the side of the channel adjacent to the reactor R, collects the nitro derivative phase 21 which is lighter, whilst the other half-channel 23b collects the heavier acid phase 22 which passes below the channel. Extensions of the half-channel convey the products to the adjacent pieces of equipment. The separator can be emptied rapidly in the case of danger by opening a valve 25 in a discharge conduit 24.

The reaction mixture can also be made to flow in a desired direction by locating a compressed air injection pump in the reactor R.

Some operational characteristics of a typical installation as shown in FIG. 1 are given below, this installation comprising 450 liter reactors and 150 liter separators. The following table gives the temperatures recorded in the various reactors of this installation during operation.

| Reactor reference number | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|---|
| Temperature (° C) | 40 | 65 | 85 | 85 | 85 | 85 | 90 | 95 | 95 | 100 | 100 | 85 |

The table below gives the rates at which reagents were supplied to the various pieces of equipment in this installation.

| Equipment reference number | $S_0$ | $R_1$ | $R_2$ | $R_3$ | $R_4$ | $R_4$ | $R_7$ | $R_7$ | $R_{10}$ | $R_{10}$ |
|---|---|---|---|---|---|---|---|---|---|---|
| Nature of the reagent | mono-nitro-toluene | water | 50–55% aqueous nitric acid | 50–55% aqueous nitric acid | sulphuric acid | concentrated nitric acid | sulphuric acid | concentrated nitric acid | sulphuric acid | nitric acid |
| Flow rate (1/hour) | 300 | 50 | 60 | 100 | 540 | 150 | 270 | 60 | 270 | 40 |

The table below gives the nitric acid concentrations measured in various separators of this equipment.

| Separator reference number | $S_3$ | $S_4$ | $S_5$ | $S_6$ |
|---|---|---|---|---|
| Concentration of nitric acid (%) | 2 | 5 | 4 | 3 |

The "wet" melting points of the nitro derivatives (mixture of dinitrotoluene and trinitrotoluene) which separated out in the separators of the trinitration section are also given below.

| Separator reference number | $S_4$ | $S_5$ | $S_6$ |
|---|---|---|---|
| Melting point (° C) | 64 | 72.5 | 74.5 |

After the nitro derivative recovered at the outlet of the separator $S_6$ had been treated with fused sulphite, it had a melting point greater than or equal to 80.2° C, which corresponds to grade I trinitrotoluene.

Typical figures for the total consumption of starting material in an installation using sulphuric acid, such as that shown in FIG. 1, in order to produce 1,000 kg of grade I trinitrotoluene, are given in the table below:

| Starting material | Consumption |
|---|---|
| Toluene | 500 kg |
| Sulphuric acid | 4,000 kg |
| Concentrated nitric acid | 900 kg |
| Dilute nitric acid | 200 kg (of $HNO_3$) |

This illustration has a production capacity of 11 tons of grade I trinitrotoluene per day.

The installation shown in FIG. 2, which also operates with concentrated sulphuric acid, is a variant of the installation of FIG. 1.

It will be seen that in this Figure an additional stage formed by a reactor $R_1$ and a separator $S_1$ has been added to the dinitration section 1. In this case, water for cooling is introduced into a coil (not shown) located in the reactor $R_2$ and 50–55% aqueous nitric acid for dinitration is introduced into the reactors $R_3$ and $R_4$.

The last stage of the trinitration section 2 comprises two additional reactors $R_{13}$ and $R_{14}$, sulphuric acid and nitric acid still being supplied to the first reactor $R_5$, $R_8$ and $R_{11}$ of each stage.

Some operational characteristics of an installation as shown in FIG. 2 are given below. The following table gives the temperatures recorded in the various reactors of this installation during operation.

An installation of this type has a capacity for producing 15 tons of trinitrotoluene per day.

The installation shown in FIG. 1 or 2 can also be operated with fuming sulphuric acid, subject to minor modifications.

In order to be able to use these installations with fuming sulphuric acid, it is sufficient to replace the first reactors of each trinitration state (supplied with nitric acid and sulphuric acid in the above-mentioned processes) by mixers $M_1$ and $M_2$ (see FIGS. 3 and 4) in which fuming sulphuric acid and concentrated nitric acid are mixed before being introduced into the reactors $R_4$ and $R_6$ (or $R_5$ and $R_7$ in the installation shown in FIG. 4).

| Reactor reference number | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|---|---|---|---|
| Temperature (° C) | 40 | 50 | 65 | 80 | 85 | 85 | 90 | 90 | 90 | 95 | 95 | 95 | 100 | 100 | 85 |

The table below gives the rates of supply to the various pieces of equipment in this installation.

| Equipment reference number | $S_0$ | $R_2$ | $R_3$ | $R_4$ | $R_5$ | $R_5$ | $R_8$ | $R_8$ | $R_{11}$ | $R_{11}$ |
|---|---|---|---|---|---|---|---|---|---|---|
| Nature of the reagent | mono-nitrotoluene | water | 50–55% aqueous nitric acid | 50–55% aqueous nitric acid | sulphuric acid | concentrated nitric acid | sulphuric acid | concentrated nitric acid | sulphuric acid | concentrated nitric acid |
| Flow rate (l/hour) | 450 | 80 | 100 | 100 | 650 | 180 | 320 | 70 | 320 | 50 |

The table below gives the nitric acid concentrations measured in the various separators of this installation.

| Separator reference number | $S_4$ | $S_5$ | $S_6$ | $S_7$ |
|---|---|---|---|---|
| Concentration of nitric acid (%) | 2 | 5 | 4 | 3 |

The "wet" melting points of the nitro derivatives which separated out in the separators of the trinitration section are also given below.

| Separator reference number | $S_5$ | $S_6$ | $S_7$ |
|---|---|---|---|
| Melting point (° C) | 56 | 70 | 74.5 |

After the product recovered in the separator $S_7$ had been treated with fused sulphite, it had a melting point greater than or equal to 80.2° C, which corresponds to grade I trinitrotoluene.

The number of trinitration stages must be reduced to two, on the one hand, because the amount of fuming sulphuric acid employed is smaller than the amount of sulphuric acid, and, on the other hand, because there is no question of the acids being too dilute in the case of fuming sulphuric acid.

A reactor $R_8$ can thus be substituted for the separator $S_5$ in the installation shown in FIG. 1 (and likewise, the separator $S_6$ of FIG. 2 can be replaced by a reactor $R_9$).

The dinitration section 1 remains identical in both cases and the connection to the trinitration stages is made between the last dinitration separator $S_3$ or $S_4$ and the first trinitration reactor $R_4$ (or $R_5$ in FIG. 4).

Some operational characteristics of installations as shown in FIGS. 3 and 4, are given below, the fuming sulphuric acid used containing 25% or $SO_3$.

The following tables give the temperatures recorded in the various reactors of these installations during operation.

a) Installation of FIG. 3:

| Reactor reference number | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| Temperature (° C) | 40 | 85 | 85 | 85 | 85 | 90 | 95 | 95 | 100 | 100 | 85 | b) Installation of FIG. 4:

| Reactor reference number | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | $R_{13}$ | $R_{14}$ |
|---|---|---|---|---|---|---|---|---|---|---|---|---|---|---|
| Temperature (° C) | 40 | 65 | 80 | 85 | 85 | 85 | 90 | 90 | 95 | 95 | 95 | 100 | 100 | 85 |

The tables below give the rates of supply to the various pieces of equipment in these installations.

a) Installation of FIG. 3.

| Equipment reference number | $S_0$ | $R_1$ | $R_2$ | $R_3$ | $M_1$ | $M_1$ | $M_2$ | $M_2$ |
|---|---|---|---|---|---|---|---|---|
| Nature | mono- | water | 50–55% | concen- | fuming | concen- | fuming | concen- |

-continued

| | | | | | | | | |
|---|---|---|---|---|---|---|---|---|
| of the reagent | nitro-toluene | | aqueous nitric acid | trated nitric acid | sul-phuric acid | trated nitric acid | sul-phuric acid | trated nitric acid |
| Flow rate (l/hour) | 300 | 20 | 160 | 40 | 340 | 100 | 230 | 50 |
| b) Installation of FIG. 4. | | | | | | | | |
| Equipment reference number | $S_0$ | $R_1$ | $R_2$ | $R_3$ | $R_4$ | $M_1$ | $M_1$ | $M_2$ | $M_2$ |
| Nature of the reagent | mono-nitro-toluene | water | 50–55% aqueous nitric acid | 50–55% aqueous nitric acid | concen-trated nitric acid | fuming sul-phuric acid | concen-trated nitric acid | fuming sul-phuric acid | concen-trated nitric acid |
| Flow rate (l/hour) | 450 | 30 | 100 | 150 | 60 | 420 | 150 | 400 | 70 |

The tables below give the nitric acid concentrations measured in the various separators of these installations.

a. Installation of FIG. 3:

| Separator reference number | $S_2$ | $S_3$ | $S_4$ | $S_5$ |
|---|---|---|---|---|
| Concentration of nitric acid (%) | 2 | 3 | 4 | 4 | b. Installation of FIG. 4:

| Separator reference number | $S_3$ | $S_4$ | $S_5$ | $S_6$ |
|---|---|---|---|---|
| Concentration of nitric acid (%) | 2 | 3 | 4 | 4 |

The "wet" melting points of the nitro derivatives which separated out in the separators of the trinitration section, are given in the tables below.

a. Installation of FIG. 3:

| Separator reference number | $S_4$ | $S_5$ |
|---|---|---|
| Melting point (° C) | 66 | 74.5 | b. Installation of FIG. 4:

| Separator reference number | $S_5$ | $S_6$ |
|---|---|---|
| Melting point (° C) | 58 | 74.5 |

After the product recovered in the separator $S_5$ of the installation of FIG. 3 and in the separator $S_6$ of the installation of FIG. 4 had been treated with fused sulphite, it had a melting point greater than or equal to 80.2° C, which corresponds to grade I trinitrotoluene.

Typical figures for the total consumption of starting materials in an installation as shown in FIG. 3 using fuming sulphuric acid in order to produce 1,000 kg of grade I trinitrotoluene, are given in the table below:

| Starting material | Consumption |
|---|---|
| Toluene | 480 kg |
| Fuming sulphuric acid | 2,500 kg |
| Concentrated nitric acid | 650 kg |
| Dilute nitric acid | 200 kg |

| Starting material | Consumption |
|---|---|
| | (of $HNO_3$) |

This installation has a production capacity of 11 tons of grade I trinitrotoluene per day, whilst the installation shown in FIG. 4 has a production capacity of 16 tons of grade I trinitrotoluene per day.

As the above description shows, the process according to the invention using either sulphuric acid or fuming sulphuric acid enables grade I trinitrotoluene to be obtained after simple treatment with fused sulphite.

The process differs from known techniques in requiring a smaller total number of pieces of equipment and in supplying a smaller number of reactors with nitric acid.

The process is simpler to carry out since the flow rates are more stable and therefore easier to control and requires approximately half the manpower to produce an identical amount of trinitrotoluene.

We claim:

1. The process for the continuous production of trinitrotoluene by nitration of dinitrotoluene in the presence of concentrated nitric acid and concentrated sulphuric acid or fuming sulphuric acid, wherein the nitration step is carried out in at least two reaction stages, said sulfuric acid and said nitric acid flowing in co-currently therein, each stage having at least two nitration zones in series followed by a separation zone, the first of said nitration zones of each stage is supplied separately with said mixture of concentrated sulphuric acid or fuming sulphuric acid and nitric acid, the total amount of said concentrated sulphuric acid or fuming sulphuric acid and nitric acid is distributed in said at least two reaction stages and trinitrotoluene is separated from said acids in each separation zone, the amount of nitric acid and sulphuric acid being so controlled that when the reaction mixture reaches each separation zone it is depleted to such an extent in nitric acid that essentially no nitration reaction occurs in each separation zone.

2. The process according to claim 1, in which said dinitrotoluene is prepared by nitration of mononitrotoluene with a mixture of sulfuric acid and nitric acid in at least three stages and each stage comprises at least one nitration zone and one separation zone, and the mixture of nitric acid and sulfuric acid which is separated in the separation zone of each nitration stage in the nitration to trinitrotoluene is recycled to the last nitration zone in the nitration of mononitrotoluene to dinitrotoluene.

3. The process according to claim 1, in which the nitric acid used to supply the nitration zone has a concentration of at least 98% by weight.

4. The process according to claim 1, in which the sulphuric acid used has a concentration of at least 96% by weight and said nitration comprises at least three stages.

5. The process according to claim 1, in which fuming sulphuric acid is used and the fuming sulphuric acid and nitric acid are introduced separately into a mixing zone and the mixture thereof is introduced into the first nitration zone of each stage.

6. The process according to claim 1, in which the rate at which sulphuric acid or fuming sulphuric acid and nitric acid are supplied to the first nitration zone of the first stage is substantially equal to the sum of the rates at which sulphuric acid and nitric acid are supplied to the nitration zones of the other stages.

7. The process according to claim 1, in which the concentration by weight of nitric acid in the sulphuric acid and niric acid mixture which is supplied to the nitration zones is from 8 to 15% by weight and the concentration of nitric acid in each separation zone does not exceed 5%.

* * * * *